(12) United States Patent
Eiff et al.

(10) Patent No.: US 7,335,876 B2
(45) Date of Patent: Feb. 26, 2008

(54) SCANNING DEVICE FOR CARRYING OUT A 3D SCAN OF A DENTAL MODEL, SLIDING PANEL THEREFORE, AND METHOD THEREFOR

(75) Inventors: Wolfgang Eiff, Heppenheim (DE); Peter Fornoff, Reichelsheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 105 days.

(21) Appl. No.: 11/253,562

(22) Filed: Oct. 20, 2005

(65) Prior Publication Data

US 2006/0102833 A1 May 18, 2006

(30) Foreign Application Priority Data

Nov. 12, 2004 (DE) .................... 10 2004 054 876

(51) Int. Cl.
*H01J 3/14* (2006.01)
(52) U.S. Cl. .................... 250/234; 250/239; 29/896.1; 29/896.11
(58) Field of Classification Search ................ 250/239, 250/208.1, 234, 235; 356/601, 602, 608; 29/896.1, 896.11, 407.04; 433/29
See application file for complete search history.

(56) References Cited

U.S. PATENT DOCUMENTS

| | | | | |
|---|---|---|---|---|
| 5,548,405 A | * | 8/1996 | Motosugi | ................ 356/601 |
| 5,671,056 A | * | 9/1997 | Sato | ................ 356/602 |
| 6,287,121 B1 | * | 9/2001 | Guiot et al. | ................ 433/218 |
| 7,010,150 B1 | | 3/2006 | Pfeiffer et al. | |
| 2003/0068079 A1 | | 4/2003 | Park | |
| 2004/0201856 A1 | | 10/2004 | Quadling et al. | |
| 2005/0060868 A1 | * | 3/2005 | McMurtry | ................ 29/559 |

FOREIGN PATENT DOCUMENTS

| | | |
|---|---|---|
| DE | 4301538 | 7/1994 |
| DE | 19709215 | 9/1998 |
| GB | 2397896 | 8/2004 |
| JP | 09178437 | 7/1997 |
| WO | WO 0228309 A1 * | 4/2002 |

OTHER PUBLICATIONS

English Abstract of DE 19709215.
English Abstract of De 4301538.
English Abstract of JP 9178437.

* cited by examiner

*Primary Examiner*—Georgia Epps
*Assistant Examiner*—Stephen Yam
(74) *Attorney, Agent, or Firm*—Dykema Gossett PLLC (57) ABSTRACT

A scanning system for carrying out a 3D scan of a tooth model includes an imaging device and a positioning system in the form of a sliding panel which can be positioned and has first locking means. On the locking panel there are provided second locking means which interact with the first locking means such that the sliding panel can assume one of several specified positions relative to the locking panel and locks in the selected position. The sliding panel has means for mounting a dental model and stands on projections disposed on its underside. A 3D scan of a tooth model is provided by creating a first image of the object to be scanned at a precisely defined locked position, moving the sliding panel to at least one further precisely defined locked position and creating another image at each such position, and creating a 3D data set by evaluating the images produced at least two different, precisely defined positions.

32 Claims, 6 Drawing Sheets

SCANNING DEVICE FOR CARRYING OUT A 3D SCAN OF A DENTAL MODEL, SLIDING PANEL THEREFORE, AND METHOD THEREFOR

BACKGROUND OF THE INVENTION

1. Field of the Invention

The invention relates to a scanning device for carrying out three dimensional scanning of dental models, to a sliding panel therefor, and to a method therefor.

2. The Prior Art

The extraoral scanning of dental impressions or models made from dental impressions with stationary scanning devices is disclosed in the prior art. The object to be scanned is usually larger than the range of image detection of the image detecting unit. It is therefore necessary to create images of the object to be scanned in several segments and to reposition the image detecting unit relatively to the object to be scanned for each image.

A device for determining the shape of a duplicate that contains a clamping device, a sensor contrivance, and a data storage unit, and in which the clamping device and the sensor contrivance are movable relatively to each other, is disclosed in EP 0 913 130 A1.

The individual images are joined together by means of software correlation. In this process, the software attempts to find the same identifying points in two different images and thereby establish a position relationship between the images. Due to imaging properties and other software-related inaccuracies incurred during the software correlation, errors cannot, in practice, be avoided when joining two correlated images. In the worst case, these errors can summate when a series of images are joined together.

Furthermore, the technical computation requirements for correlating images with unknown misalignment are very great, which results in a long processing time.

It is thus an object of the invention to provide a scanning device, as well as a method of scanning dental models, that permits rapid and exact scanning of dental models and is in addition cheap to produce in comparison with prior art devices.

SUMMARY AND OBJECTS OF THE INVENTION

This object is achieved by a scanning device as defined in claim 1 and by a method of scanning dental models as defined in claim 15. Advantageous developments are described in the subclaims.

The scanning device of the invention for carrying out 3D scanning of dental models consists of an imaging device and a positioning system, in which the positioning system contains a panel that is adjustable in relation to the imaging device and on which the object to be scanned can be fixed. The adjustable panel is slid along a base plate that is stationary relative to the imaging device. The panel is in the form of a sliding panel and contains a first set of locking means. The base plate is in the form of a locking panel and has a second set of locking means, which interacts with the first set of locking means in such a manner that the sliding panel can assume a plurality of specific positions relative to the locking panel and can be locked in the selected position.

In a scanning device thus constructed, the adjustable panel can only assume exactly defined positions. There is thus a finite number of displacement vectors between individual images, which reduces the correlation of the various images to a discrete number of correlation possibilities. In this manner, the number of computations required is substantially reduced. Furthermore, there is no longer any propagation of summed correlation errors. The scanning results are thus more accurate than when scanning according to the prior art.

The imaging device is advantageously in the form of an image detecting unit. It is then possible to make a three dimensional scan without resorting to mechanical probing methods.

It is particularly advantageous if the range of image detection of the image detecting unit is smaller than the object to be scanned. Such image detecting units can be produced very economically, because the resolution of the image sensor and/or the size of the optics can be kept small, which allows for an economic construction using standard components.

An additional particularly advantageous embodiment of the invention relates to the use of an oral scanning camera for detecting the image. Oral scanning cameras are known in the prior art and, because conventional parts may be used and the design costs are less, a scanning device using an oral scanning camera can be sold cheaper than a scanning device incorporating a custom designed image detection device.

The scanning device is advantageously equipped with a light filter that screens the window through which light passes in and out, from the ambient light. Ambient light reduces the quality of the images and consequently the quality of the scan data. The light filter can be attached such that it also protects the lens of the scanning device from mechanical damage. This is accomplished by attaching the light filter in front of the lens.

The scanning device, in particular an oral scanning camera, operates advantageously with a telecentric optical path. A telecentric optical path has the advantage that the image of the object is always the same size regardless of the distance of the object from the lens. This property makes it easier to analyze a telecentric image.

Advantageously, the distance from the image detecting unit from the sliding panel is adjustable. The depth of focus of all optical imaging systems is limited by physical laws. Since not all objects to be scanned are in practice of the same height, it may be necessary to adjust the image detecting device such that the sharp layer lies on the surface of the object to be scanned.

Advantageously, means are provided for measuring the distance of the image detecting unit from the locking panel. Even with telecentric beam paths it may be necessary in some cases to know the relative distance from the image detecting unit to the object to be scanned, for example, in order to correlate successive images that were created at different camera heights.

The spacing between the locked positions in directions X and Y are advantageously selected so that it is smaller than, or the same as, the range of image detection of the image detecting device and larger than half of the range of image detection in the respective direction. The spacing should be selected such that there is seamless joining or overlapping of images created at adjacent locked positions, so that the images can be joined together with no gaps and that the overlap zone is small enough to ensure efficient scanning of the area being scanned involving as few images as possible.

It is particularly advantageous if the intervals between the locked positions in the X and Y directions are selected so that the image zones scanned in adjacent positions overlap by at least one tenth of the range of image detection. This degree of overlap is sufficient to identify identical areas in adjacent images and thus ensure correlation.

One of the locking means is advantageously in the form of a projection and the other locking means is advantageously in the form of a depression. Such locking means can be produced by simple production techniques but still exhibit a high degree of precision.

Either the sliding panel or the locking panel is advantageously equipped with three projections. A three point means of support ensures a steady and firm table-top for the sliding panel.

The projections advantageously have substantially convex bearing surfaces. Such projections are resistant to deformations and usually have a point of support that can be defined exactly.

The depressions are advantageously in the form of grooves. The sliding panel can then be slid easily in one direction, because at least one of the projections slides in one of the grooves as the sliding panel is slid.

The land between two grooves is advantageously convex. This makes it almost impossible, in practice, to position the sliding panel incorrectly, as gravity causes the projection to slip automatically into the groove.

It has been found to be particularly advantageous if the second locking means are divided into a first area containing parallel, equidistantly spaced grooves and a second area containing parallel, equidistantly spaced grooves, and the grooves of the first area are substantially at right angles to the grooves of the second area. As a result, the sliding panel can only be slid in the X and Y directions. Furthermore, it is particularly easy to manufacture such an interlocking system.

The sliding panel is advantageously equipped with a device for adjusting the angle of the object to be scanned.

Sometimes it is necessary not only to scan objects from a specific direction but also to move the object into a different position relative to the image detecting unit, as some objects have undercuts that cannot be scanned in any other way.

The sliding panel is advantageously provided with marks, and the position of said marks corresponds to the position of the first locking means on the underside of the panel. The operator of the scanning system can thus easily check the position of the first locking means on the locking panel.

It is particularly advantageous if the locking panel has at least one through hole for securing an object to be scanned, which will be held immobile and scanned in the X and Y directions, and the planar extent of the object to be scanned is smaller than the range of image detection of the image detecting unit. The object is secured by fastening means, and the fastening means and the through hole are aligned so that the object lies in the same range of image detection as the object to be scanned that is positionable with the sliding panel. The object can also be aligned at an angle, for which a second through hole can be provided to ensure that the object still lies in the range of image detection in spite of being positioned at an angle.

The scanning device is advantageously equipped with an evaluation unit that computes a 3D data set based on the image data. A 3D data set can thus be generated immediately after scanning.

The distance between the locked positions of the sliding panel on the locking panel can be advantageously stored in the evaluation unit and the evaluation unit computes the 3D data set based on the scan data and said known distance.

The scanning device is advantageously calibrated by using a calibration body of known geometry, and the calibration data are stored in memory in the evaluation unit and used to analyze the images. The scanning device consists of a plurality of parts, the exact assemblage of which relative to each other may vary from device to device due to manufacturing tolerances. Calibration is therefore advantageous to ensure the accuracy of the analysis.

The alignment of the image detecting unit relative to the directions of displacement of the sliding panel is advantageously determined during calibration. Possibly, the displacement directions and the long sides of the image detector in the image detecting unit will not be exactly parallel. A movement of the sliding panel will then be recorded as an angular displacement, which will be allowed for during correlation of adjacent images by reference to the calibration data.

The spatial alignment of the locking panel relative to the image detecting unit is advantageously determined during calibration. If the planes of the locking panel and the imaging detector in the image detecting unit are not absolutely parallel, a movement of the sliding panel on the locking panel will also change the distance between the object to be scanned and the image detecting unit.

The change of the range of image detection when changing the height of the image detecting unit above the locking panel is advantageously determined during calibration. The optical path of the image detecting unit of an oral scanning camera is not necessarily perpendicular to the direction of displacement of the image detecting unit when there is a change in the height of the image detecting device. In this way, different image segments will be imaged at different heights.

Advantageously, there are means on the locking panel for determining the position of the sliding panel. This facilitates the automatic association of images which have been created at different positions of the sliding panel.

The surface of the sliding panel and/or the locking panel is advantageously provided with a layer having good sliding properties. This makes it more difficult to position the sliding panel incorrectly, and, in addition, operation thereof is easier. In addition, the layer can be scratch proof in order to ensure a long useful life.

It is particularly advantageous if the scanning device is equipped with a display device on which the images generated by the image detecting unit can be displayed. The display device can then continuously display the current portion of the image in the image detecting device and the user can then position the object to be scanned as desired and adjust the sharp layer of the image detecting unit prior to image creation.

The locking panel used is advantageously replaceable. It is then possible to replace a damaged locking panel or install an improved locking panel, if available.

An additional object of the invention relates to a sliding panel for use in a dental scanning device in which the upper surface of the sliding panel has a fastening means for a dental model and in which the bottom surface of the sliding panel has projections on which the sliding panel rests. Such a sliding panel can be freely positioned within the limits imposed by the dental scanning device. The sliding panel can be removed from the scanning system and a dental model can be fixed thereon. Such fastening away from the image detecting unit is easier to accomplish.

The fastening means is advantageously rotatable and tiltable. This allows for a wider working zone, as a dental model to be scanned can then be scanned from different directions and undercuts can be avoided.

Marks corresponding to the position of the projections on the underside of the sliding panel are advantageously provided on the upper surface of the sliding panel. The user can then easily check the position of the points of support.

Advantageously there are three projections, of which two are aligned parallel to one edge of the sliding panel. This results in a preferential direction of displacement parallel to the edge of the sliding panel.

An additional object of the invention relates to a method for carrying out a 3D scan of dental models. A first image of the object to be scanned is produced, for which purpose the sliding panel is placed in a first position as set by the locking means. Then an additional image is produced in at least one more position as set by the locking means. This step can be repeated as often as necessary until the object is scanned in its entirety. Finally, a 3D data set is computed by analyzing the positions from the at least two different images from the preceding step and accounting for the positions set by the locking means. The production of a 3D scan of dental models by this procedure is very reliable and the risk of errors is negligible.

The scanned image segment is advantageously checked by a user on a display device prior to the creation of each image and the height of the imaging unit is adjusted so as to position the sharp layer such that the region to be imaged yields a sharp image. This ensures a sharply focused image of all scan-relevant data and thus a high degree of accuracy.

The imaging unit is advantageously equipped with means for determining the sharp image area and means for adjusting the sharp image area, by which means the imaging unit will automatically adjust the sharp image area. This ensures that the optimum sharp image area is set each time and prevents incorrect operation.

The spacing between the locked positions of the sliding panel is advantageously programmed into the evaluation unit and the images are joined together by the evaluation unit with an offset specified by said spacing between the locked positions of the sliding panel. With such a procedure it is no longer necessary to correlate adjacent images, so that no propagation of errors occurs. The assembled scan data are thus more exact than independently correlated images.

The evaluation unit advantageously compares the individual images with each other in a marginal region in order to determine the relative positions of the images. In this manner the evaluation unit can automatically recognize adjacently positioned images and join them together correctly.

A calibration of the scanning device is advantageously performed by scanning a calibration body on a sliding panel in several positions thereof and allowing the evaluation unit to analyze the images at said positions and compute calibration data therefrom and store the same in memory. This ensures an optimum of scanning accuracy in spite of manufacturing tolerances.

An offset of the image segment resulting from a height adjustment of the image detecting unit is advantageously automatically corrected by the evaluation unit. To do this, the evaluation unit implements the direction of displacement which was determined during calibration of the scanning device and which indicates the offset of two images created at different heights which is required in order to move the same image segments of two images scanned in adjacent positions along the direction of displacement so that the two images match each other in the marginal region as far as possible. This also compensates for any possible vertical offset of the images relative to each other as a result of imaging at different heights.

The single images are advantageously combined in a composite data set. The result is then a data set containing all relevant information and optimally suitable for further processing.

BRIEF DESCRIPTION OF THE DRAWINGS

A scanning device of the invention is explained below with reference to the drawings, in which.

DETAILED DESCRIPTION OF AN EXEMPLARY EMBODIMENT OF THE INVENTION

Figure 1:
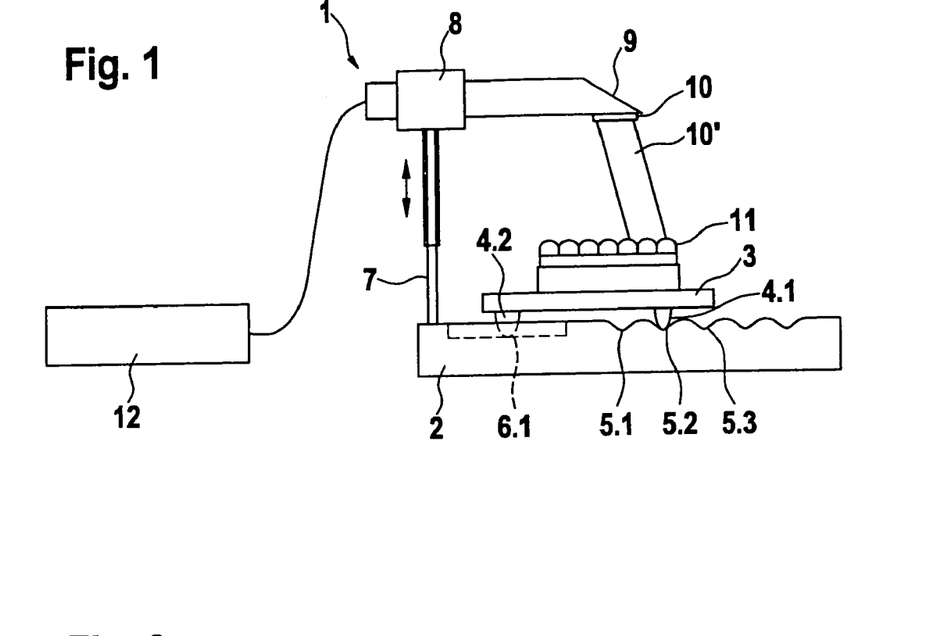
FIG. 1 is a diagrammatic representation of a three dimensional scanning device of the invention.

FIG. 1 is a diagrammatic representation of a scanning device 1 of the invention. The scanning system 1 comprises a locking panel 2, the design of which will be explained in more detail with reference to FIGS. 2 and 3. On the locking panel 2 there is a sliding panel 3 that rests on the locking panel 2 on the projections 4.1, 4.2, 4.3 (not shown). The projections 4.1 and 4.3 slide in the X direction in one of the grooves 5.1, 5.2, 5.3, while the projection 4.2 slides in the Y direction in one of the grooves 6.1, 6.2, 6.3. Engagement of the projections 4.1 and 4.3 in the groove 5.2 and that of the projection 4.2 in the groove 6.1 is illustrated here. The locking panel 2 is provided with a scratch-proof coating having good sliding properties.

On the locking panel 2 there is additionally provided a column 7, the height of which is adjustable, with a mount 8 for a scanning camera 9 which is in principle an oral scanning camera. The lens of the scanning camera 9 is fitted with a light filter 10 to shield the optics of the scanning camera from the ambient illumination. The light filter 10 also protects the exposed lens from physical damage. The scanning camera 9 points to the sliding panel 3 to which the object 11 to be scanned is fixed, and the optical path 10' is telecentric and is vertically inclined at a slight angle of up to 5 degrees, as is customary for standard oral scanning cameras.

The scanning camera 9 is connected to an evaluation unit 12 that receives, stores, and analyzes the scan data transmitted by the scanning camera.

Figure 2:
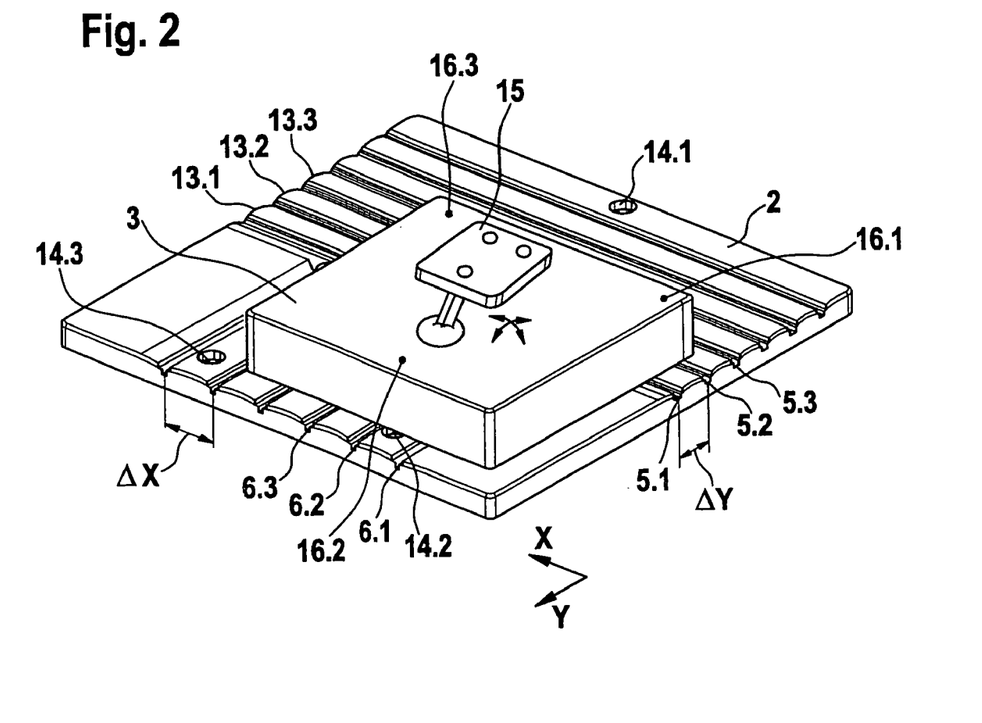
FIG. 2 is a top view of a sliding panel with a tiltable fixing element and the associated locking panel.

FIG. 2 clarifies the construction details of the locking panel 2 and the sliding panel 3. On the locking panel 2 there are two groups each of parallel equidistant grooves 5.1, 5.2, 5.3 and 6.1, 6.2, 6.3 and the two groups are substantially at right angles to each other. The lands separating the grooves, for example that between 5.1 and 5.2, designated in the figure as 13.1, are substantially convex. The locking panel 2 can be fixed to a table by way of the drill holes 14.1, 14.2, 14.3. The intervals ΔX between the grooves in the X direction 6.1, 6.2, 6.3 and ΔY between the grooves in the Y direction 5.1, 5.2, 5.3 match the range of image detection of the scanning camera 9. In this case the image detected is 17 mm long in the X direction and 14 mm wide in the Y direction. A 2 mm overlap for each marginal region is taken into account, so that ΔX in this case equals 15 mm and ΔY equals 12 mm.

A swivel-type mount 15 is attached to the sliding panel 3 which makes it possible to position an object 11 fixed thereto for scanning at any desired height, direction and angle.

Additionally, there are marks 16.1, 16.2, 16.3 on the top surface of the sliding panel 3 that correspond to the position of the points of support 4.1, 4.2, 4.3 (not shown) underneath.

Figure 3:
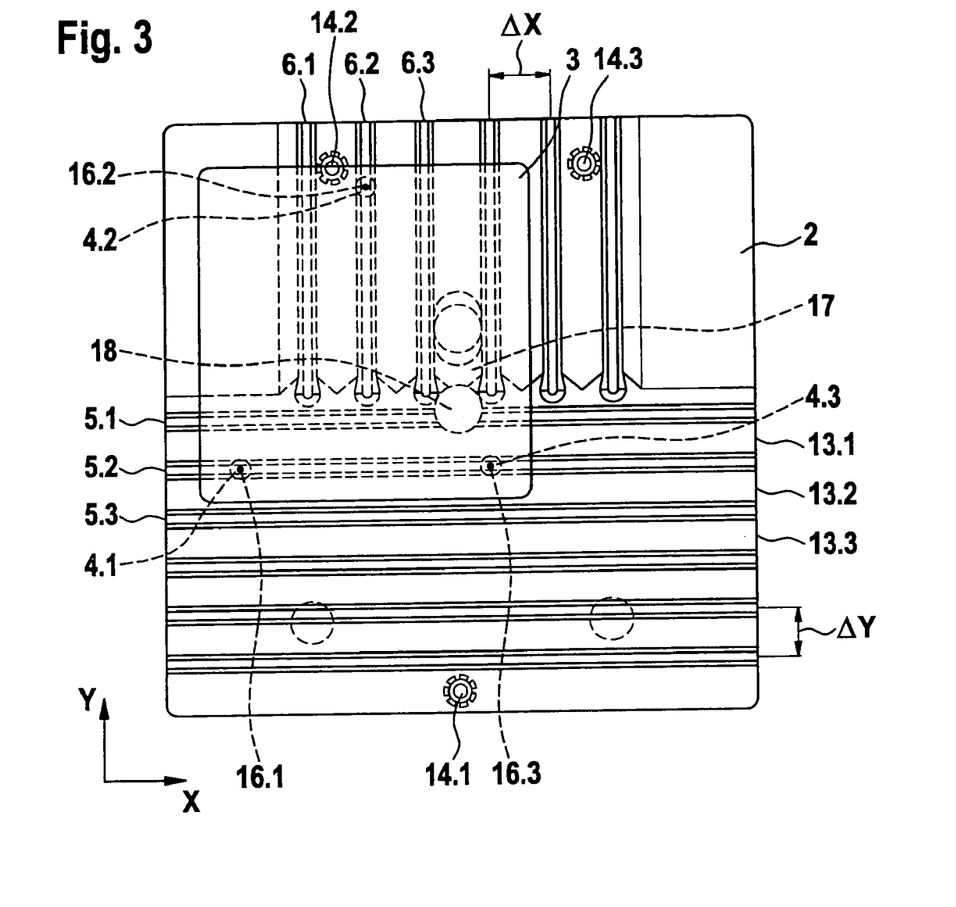
FIG. 3 is a top view of the sliding panel and the associated locking panel.

A top view of the locking panel 2 and the sliding panel 3 is illustrated in FIG. 3. Here the projections 4.1 and 4.3 are in groove 5.2, and the projection 4.2 is in groove 6.2. Following creation of an image, the sliding panel 3 can now be slid from this first position to another precisely defined position, for example in the Y direction by moving the projections 4.1 and 4.3 to the groove 5.1. During this movement, projection 4.2 remains in groove 6.2. Movement in the X direction is also possible, in which case the projections 4.1 and 4.3 will slide along the groove 5.2 while the projection 4.2 is moved to groove 6.3.

Taking all possible positions of the sliding panel into account, there results a matrix showing equal intervals in the X and the Y directions.

There is a drill hole 16 in the locking panel 2 of the sliding panel for mounting a holder. Underneath the locking panel there is provided a rotatable, upwardly inclined holder for holding an object that can be scanned in its entirety and from all sides by the scanning camera 9.

Figure 4:
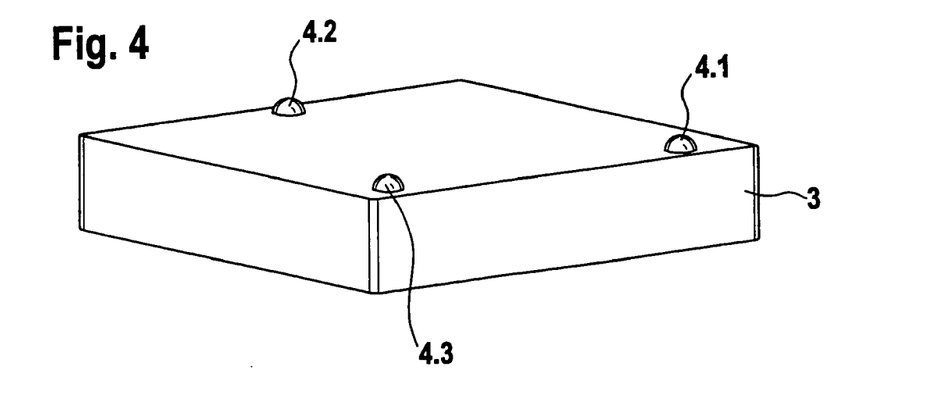
FIG. 4 is a perspective view of the underside of the sliding panel.

In FIG. 4, the sliding panel 3 is illustrated as viewed from its underside. The projections 4.1, 4.2, and 4.3 are spherical in shape. This, in conjunction with the convex ridges between the grooves, makes incorrect positioning almost impossible.

Figure 5:
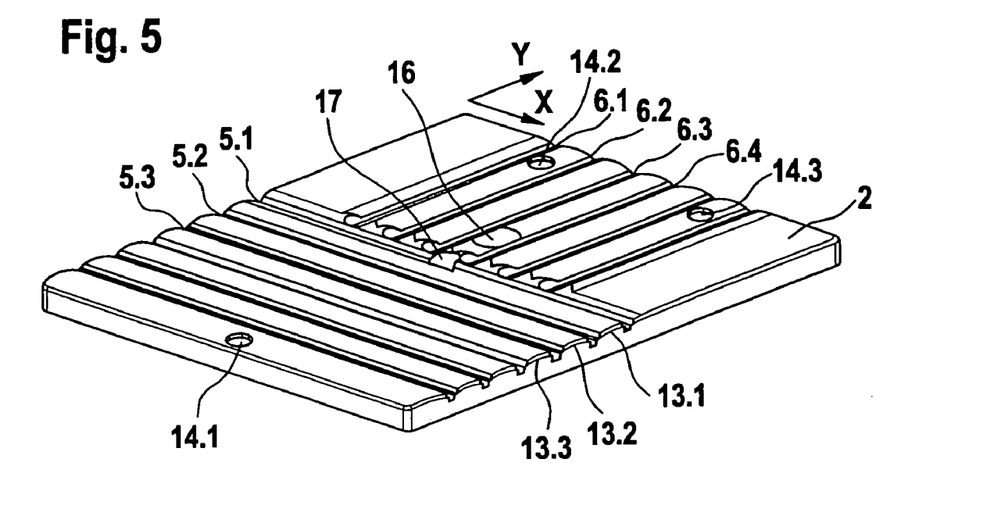
FIG. 5 is a perspective view of the locking panel without the sliding panel.

FIG. 5 is a perspective view of the locking panel of the invention. There are two through holes 16, 17 in the locking panel. These through holes 16, 17 are for the insertion of a holder on which the dental model 18 to be scanned can be mounted. The through holes are arranged such that the tooth can be positioned in the same optical path of the image detecting device through either hole by selecting a holder designed to fit properly. The through holes 16, 17 are located on the ridge between the grooves 6.3 and 6.4, making it impossible to slide the projection 4.2 into one of the through holes 16, 17 and thus to position the sliding panel incorrectly.

Figure 6:
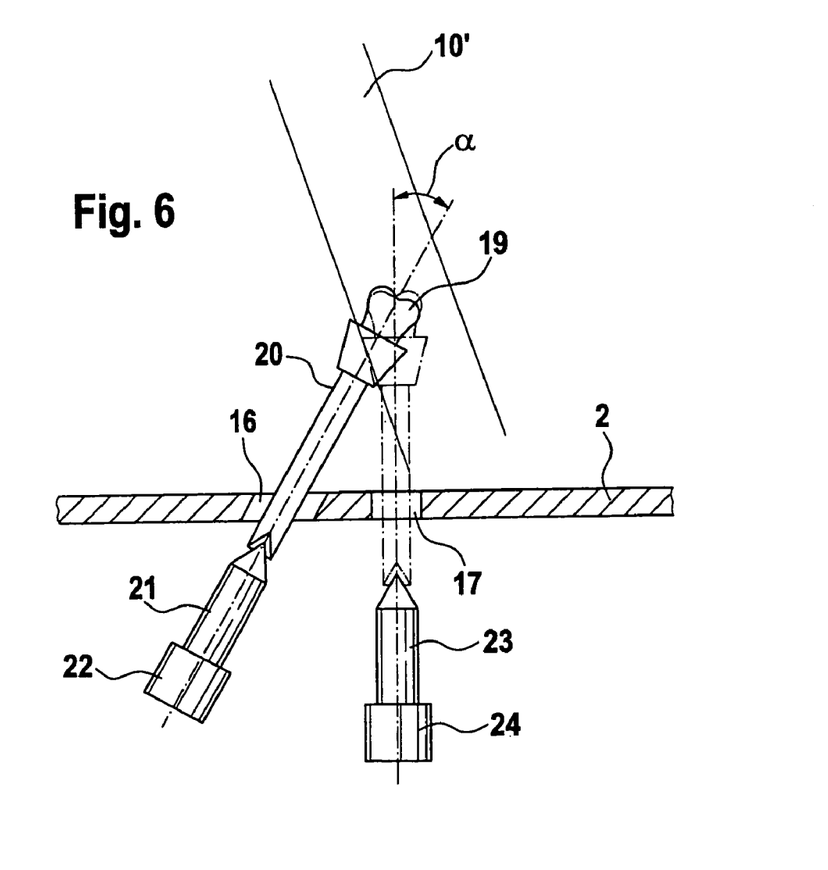
FIG. 6 illustrates the rotary scanning of objects in the scanning device.

The through hole 16 serves to hold a tooth at a specified angle α, which is in this case 30° (FIG. 6). The holder is rotatable so that the tooth can be scanned from all sides. The through hole allows the tooth to be aligned exactly perpendicular to the surface of the locking panel 2 so that scanning of any cavities on the upper surface of the dental model 18 is possible.

The function of the through hole 16, 17 and the positioning of the objects to be scanned by rotary scanning are illustrated in FIG. 6. An object 19 is fastened to a holder 20 which is pressed onto the spindle 21 of a motor 22 located underneath the locking panel 2. The object to be scanned, for example a tooth, is located in the optical path 10' of the image detecting system 9. The tooth 19 is turned progressively by the motor 22 through a specific angle of, say, 45° per step, after which an additional image is created. The angle of 30° ensures that the tooth 19 is scanned completely from all sides without any undercuts. If there are cavities on the upper surface of the tooth 19, the holder can be pressed onto the spindle 23 on the motor 24 through the through hole 17. In this manner, images of the upper surface having such cavities of the tooth 19 can be created from different directions.

Figure 7:
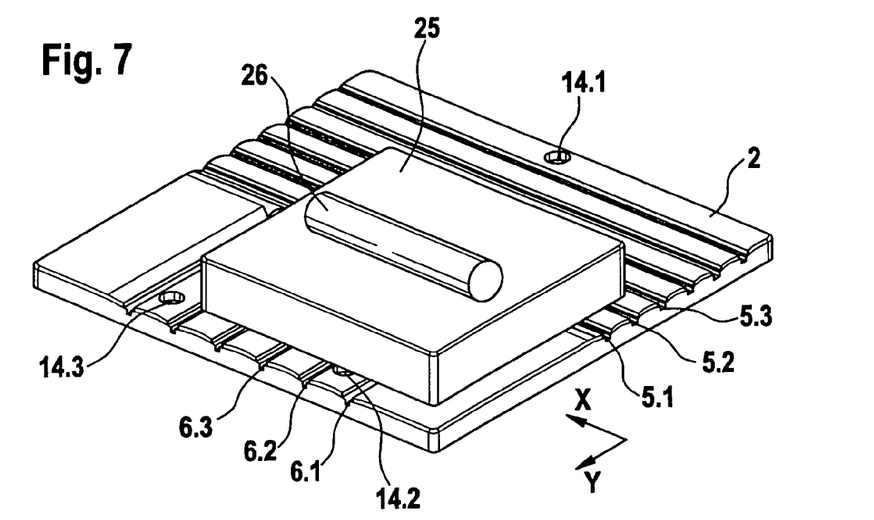
FIG. 7 shows the locking panel and a sliding panel for calibrating the system.

FIG. 7 shows a calibration system 25 having a calibration body 26 for calibrating the scanning device. For this purpose the calibration system 25, like the sliding panel, has three projections (not shown) that engage in the grooves 5.1, 5.2, 5.3 and 6.1, 6.2, 6.3 on the locking panel 2. The calibration body 26 is a cylinder made to a very high degree of precision and firmly attached to the calibration unit 25. The evaluation unit 12 is able to detect the axis of the calibration body 26 from the scan data.

Figure 8:
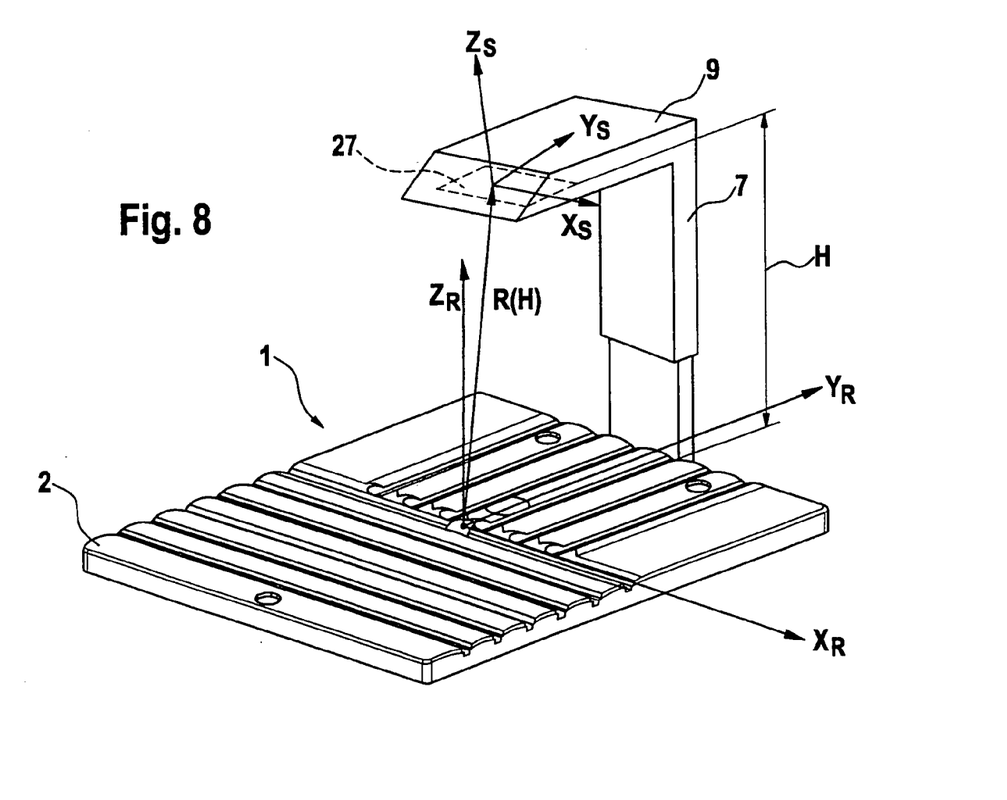
FIG. 8 shows the degrees of freedom of the scanning device which are to be calibrated.

The calibration procedure is explained below with reference to FIG. 8 and FIG. 9. The locking panel 2 of the three dimensional scanning device 1 has an alignment specified by the spatial coordinates designated $X_R$, $Y_R$ and $Z_R$. These coordinates are chosen so that $X_R$ indicates the direction of one displacement vector and $Y_R$ indicates the direction of the other displacement vector, while $Z_R$ indicates the direction of the perpendicular to the surface of the locking panel 2. Furthermore there is an additional coordinate system $X_S$, $Y_S$, $Z_S$ for the sensor 27, which is skewed relative to the coordinate system of the locking panel 2. The directions $X_S$ and $Y_S$ are parallel to the edges of the image sensor. The direction $Z_S$ defines the vector of the perpendicular to the surface of the image sensor 27. The two sets of coordinates $X_R$, $Y_R$, $Z_R$ and $X_S$, $Y_S$, $Z_S$ are skewed and tilted relatively to each other as a result of manufacturing tolerances.

The first objective of the calibration procedure is to determine the positions of the two coordinate systems relative to each other. This is accomplished by scanning the calibration unit 25 illustrated in FIG. 7 in four different positions representing the extreme positions of said calibration unit 25 on the locking panel 2. From the change in the axial position of the axis of the calibration body 26, the evaluation unit can define, on the one hand, the relative alignment of the two coordinate systems to each other and, on the other hand, the displacement vectors $X_R$ and $Y_R$ of the sliding panel 3 with respect to the position of the image sensor, given by $X_S$ and $Y_S$.

Finally an additional calibration is performed to determine the absolute position of the two coordinate systems to each other as a function of the height H of the image detecting unit from the locking panel. The vector R(H), together with the image offset caused by the inclined optical path 10', is responsible for the absolute image offset as a function of the change in height.

In order to ascertain this relationship the calibration unit 25 is placed in two positions perpendicular to each other on the locking panel 2 and scanned at two heights in each position by the image detecting system 9. The displacement vector R(H) can be unambiguously determined from the four images.

Figure 9:
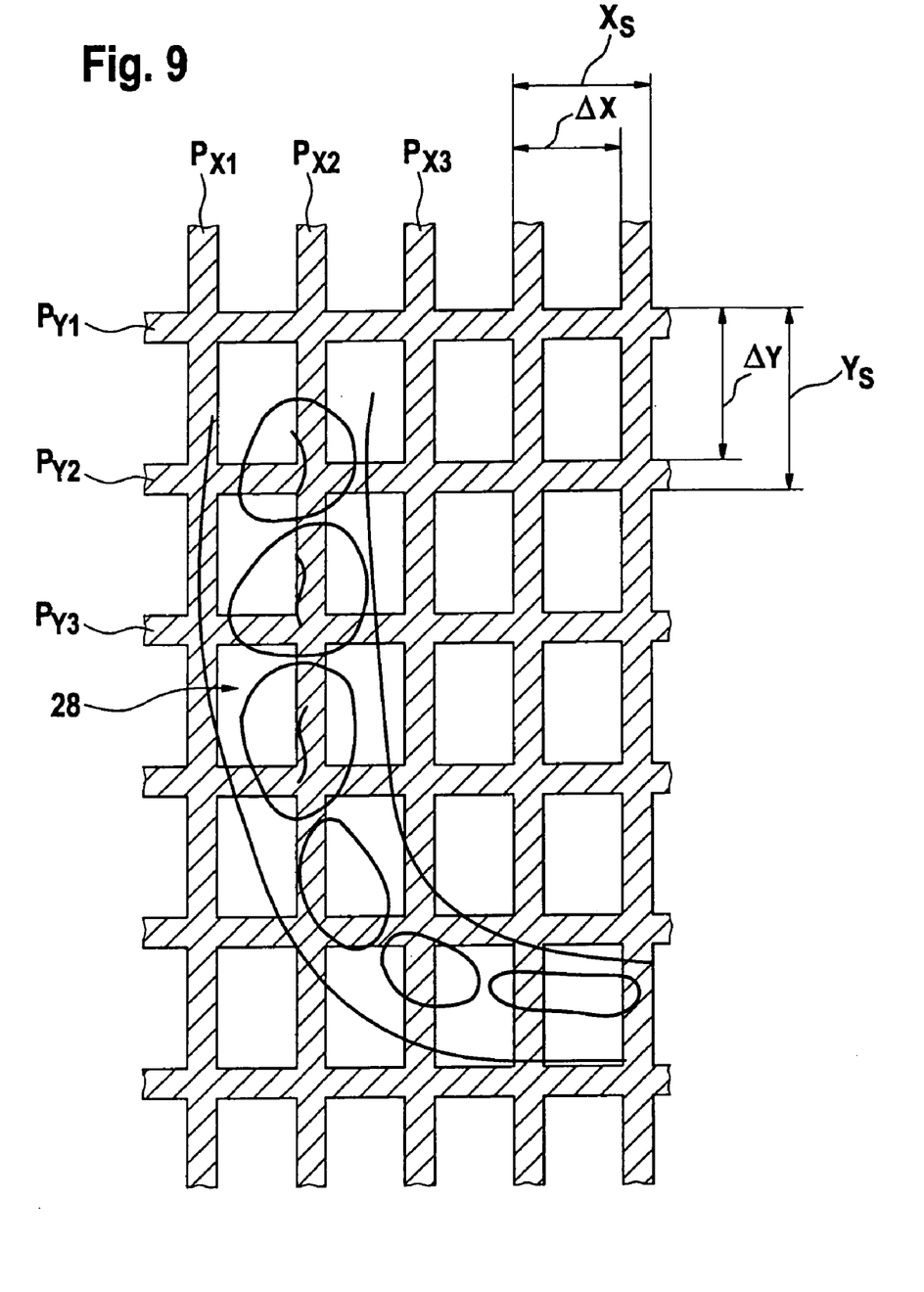
FIG. 9 illustrates the scanning zones with reference to a dental model.

FIG. 9 illustrates scanning of a dental model 28. The dental model 28 is moved together with the sliding panel 3 on the locking panel and can assume only specific positions represented here by $P_{X1}$, $P_{X2}$, $P_{X3}$ and $P_{Y1}$, $P_{Y2}$, $P_{Y3}$. The intervals ΔX in the X direction and ΔY in the Y direction are defined by the distances between the grooves. The range of image detection $X_S$, $Y_S$ of the sensor is larger than the locking intervals. This results in overlap zones in adjacent images that are illustrated here by hatching. These overlap zones are used by the evaluation unit 12 to join the corresponding single images together.

Figure 10:
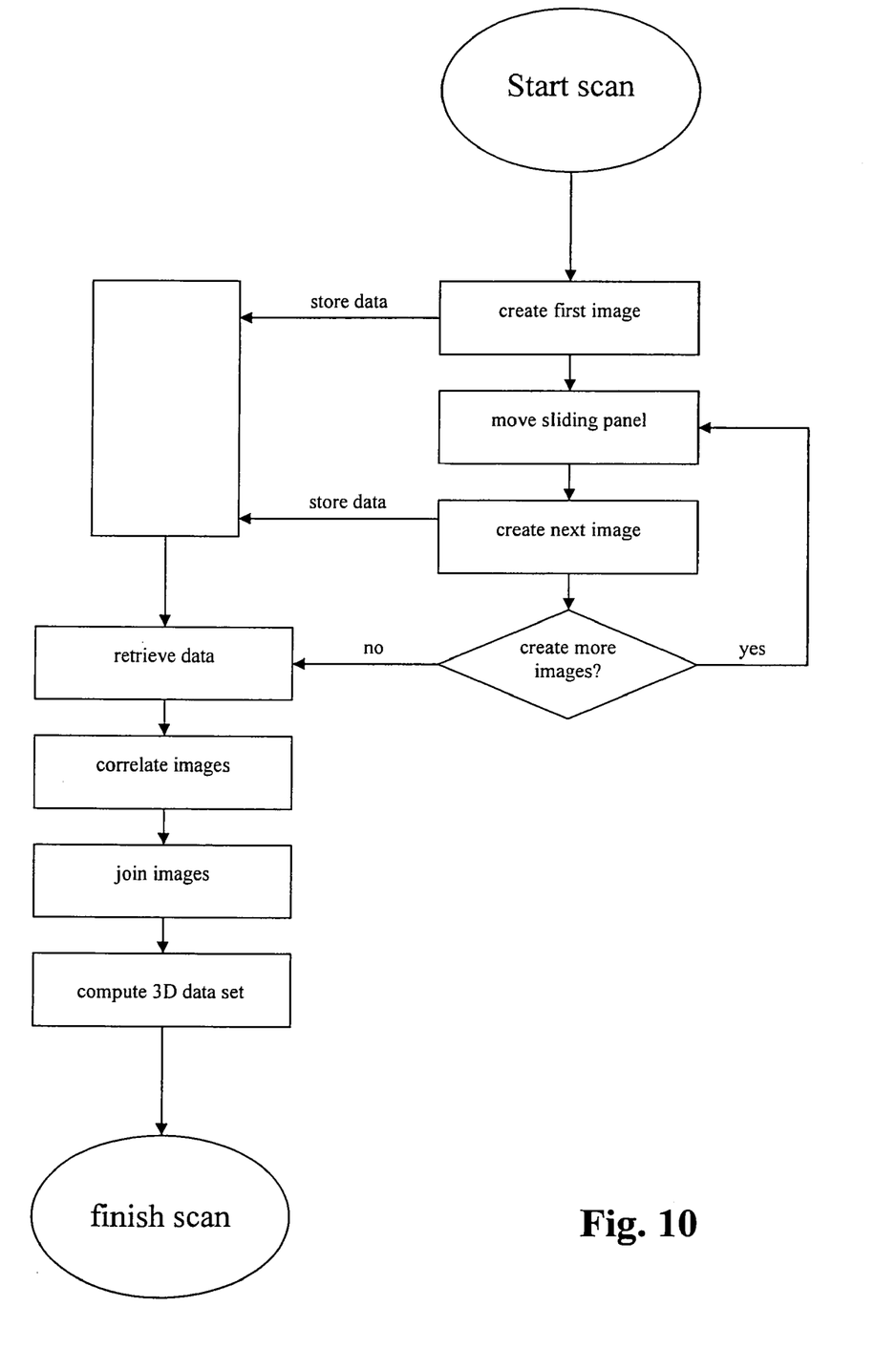
FIG. 10 illustrates the scanning method in the form of a program structure diagram.

FIG. 10 illustrates the method of the invention with reference to a flow diagram in a first position of the sliding panel for creating a first image. The image data are stored on a data medium located in the evaluation unit. Afterwards the sliding panel is moved along a groove in the X or Y direction, as explained in the above description of the drawings. Then a new image is created in this new position. The data are again stored in the data storage device of the evaluation unit. If additional images are to be made, the last step following movement of the sliding panel is repeated until the object to be scanned has been scanned in its entirety. On completion of the scan, the evaluation unit 12 retrieves the data from the data storage device, correlates the overlap zones of the individual images and joins the images together, taking into account the known distance between the grooves 5.1, 5.2 and 6.1, 6.2, and computes from all of the above a complete 3D data set.

LIST OF REFERENCE NUMERALS

| | |
|---|---|
| 1 | scanning system |
| 2 | locking panel |
| 3 | sliding panel |
| 4.1, 4.2, 4.3 | projections |
| 5.1, 5.2, 5.3 | grooves in the X direction |
| 6.1, 6.2, 6.3 | grooves in the Y direction |
| 7 | column |
| 8 | mount |
| 9 | scanning camera |
| 10 | lens protector |
| 10' | optical path |
| 11 | object to be scanned |
| 12 | evaluation unit |
| 13.1, 13.2, 13.3 | ridge |
| 14.1, 14.2, 14.3 | attachment bores |
| 15 | rotatable mount |
| 16 | through hole for rotary scanning |
| 16.1, 16.2, 16.3 | mark |
| 17 | through hole for vertical scanning |
| 18 | holder |
| 19 | tooth |
| 20 | holder |
| 21 | spindle |
| 22 | motor |
| 23 | spindle |
| 24 | motor |
| 25 | calibration device |
| 26 | calibration body |
| 27 | sensor |
| 28 | dental model |

The invention claimed is:

1. A scanning system (1) for carrying out a 3D scan of a tooth model, comprising an imaging device (9) and a positioning system (2, 3), wherein the positioning system (2, 3) comprises a sliding panel (3) with the possibility of being positioned relatively to said imaging device, to which a tooth model to be scanned can be attached, and a base plate (2) which is stationary with reference to the imaging device, wherein said sliding panel (3) includes first locking means (4.1, 4.2, 4.3) and the base plate is in the form of a locking panel (2), wherein the locking panel comprises second locking means (5.1, 5.2, 5.3, 6.1, 6.2, 6.3) which interact with the first locking means (4.1, 4.2, 4.3) such that the sliding panel (3) can assume one of several specified positions relative to the locking panel (2) and locks in a selected position.

2. A scanning system as defined in claim 1, wherein said imaging device (9) is in the form of an image detecting unit (9).

3. A scanning system as defined in claim 2, wherein the range of image detection of the image detecting unit is smaller than the object (11) to be imaged.

4. A scanning system as defined in claim 2, wherein image detection is effected using an oral scanning camera (9).

5. A scanning system as defined in claim 2, wherein the inlet/outlet window for the scanning rays is provided with a light filter (10) for cutting out ambient light.

6. A scanning system as defined in claim 2, wherein the optical path of the image detecting unit (9) is telecentric.

7. A scanning system as defined in claim 2, wherein the distance of the image detecting unit (9) from the sliding panel (3) is variable.

8. A scanning system as defined in claim 7, wherein means are provided for detecting the distance of the image detecting unit (9) from the locking panel.

9. A scanning system as defined in claim 2, wherein the spacing between the lock positions in the X and Y directions is equal to or less than the range of image detection of the image detecting unit (9) and greater than one half of said range of image detection.

10. A scanning system as defined in claim 9, wherein the spacing between the lock positions in the X and Y directions is such that the image segments created in adjacent positions overlap by at least one tenth of the range of image detection.

11. A scanning system as defined in claim 1, wherein said first locking means (4.1, 4.2, 4.3) are in the form of projections and said second locking means (5.1, 5.2, 5.3, 6.1, 6.2, 6.3) are in the form of depressions.

12. A scanning system as defined in claim 11, wherein three projections (4.1, 4.2, 4.3) are provided on said sliding panel (3) or on said locking panel (2).

13. A scanning system as defined in claim 11, wherein said projections (4.1, 4.2, 4.3) have a substantially convex bearing face.

14. A scanning system as defined in claim 11, wherein said depressions (5.1, 5.2, 5.3, 6.1, 6.2, 6.3) are in the form of grooves.

15. A scanning system as defined in claim 14, wherein the land between two grooves (5.1, 5.2, 5.3, 6.1, 6.2, 6.3) has a convex design.

16. A scanning system as defined in claim 11, wherein the second locking means (5.1, 5.2, 5.3, 6.1, 6.2, 6.3) are divided into a first region having parallel, equidistant grooves and a second region having parallel, equidistant grooves, the grooves in the first region being substantially at right angles to the grooves in the second region stand.

17. A scanning system as defined in claim 1, wherein the sliding panel (3) is provided with a device (15) for the adjustment of the degree of inclination of the object (11) to be scanned.

18. A scanning system as defined in any claim 1, wherein the visible side of the sliding panel (3) is provided with marks (16.1, 16.2, 16.3) at positions corresponding to the position of said first locking means (4.1, 4.2, 4.3) on the underside of said panel.

19. A scanning system as defined in claim 1, wherein said locking panel (3) has at least one hole (17, 18) for the attachment, by fastening means, of an object (19) to be scanned which is immobile in the X and Y directions, which fastening means (21, 23) is designed such that said object is in the same range of image detection as the displaceable object (11) to be scanned.

20. A scanning system as defined in claim 1, wherein an evaluation unit (12) is provided which computes a 3D data set on the basis of the image data.

21. A scanning system as defined in claim 20, wherein calibration of the scanning system (1) is carried out using a calibration body (25, 26) with known geometry and the calibration data determined by said calibration are implemented in the evaluation unit (12) for evaluating the images.

22. A scanning system as defined in claim 21, wherein said calibration determines the alignment of the image detecting unit (9) relative to the directions of displacement X and Y of the sliding panel (3).

23. A scanning system as defined in claim 21, wherein said calibration determines the relative spatial alignment of said locking panel (2) relative to said image detecting unit (9).

24. A scanning system as defined in claim 21, wherein said calibration determines the change in the range of image detection when the height of said image detection system (9) above said locking panel (2) is changed.

25. A scanning system as defined in claim 1, wherein said locking panel (2) is provided with means for determination of the position of said sliding panel (3).

26. A scanning system as defined in claim 1, wherein the surface of said sliding panel (3) and/or locking panel (2) is provided with a layer having good sliding properties.

27. A scanning system as defined in claim 2, wherein a display is provided on which the images produced by means of said image detecting unit can be displayed.

28. A scanning system as defined in claim 1, wherein said locking panel (2) is replaceable.

29. A scanning system according to claim 1, wherein on a top side of said sliding panel (3) there is provided attachment means (15) for attaching a tooth model (11) and furthermore projections (4.1, 4.2, 4.3) are provided on the underside of said sliding panel (3), on which said sliding panel (3) rests.

30. A scanning system as defined in claim 29, wherein said attachment means (15) is rotatable and tiltable.

31. A scanning system as defined in claim 29, wherein on the top side of said sliding panel (3) marks (16.1, 16.2, 16.3) are provided at positions corresponding to the position of said projections (4.1, 4.2, 4.3) on the underside of said panel.

32. A scanning system as defined in claim 29, wherein three projections (4.1, 4.2, 4.3) are provided, of which two projections (4.1, 4.3) are positioned such that they are parallel to an edge of said sliding panel (3).

* * * * *